United States Patent [19]

DuBois

[11] 4,353,889

[45] Oct. 12, 1982

[54] REBAUDIOSIDE ANALOGS

[75] Inventor: Grant E. DuBois, Palo Alto, Calif.

[73] Assignee: Dynapol, Palo Alto, Calif.

[21] Appl. No.: 272,799

[22] Filed: Jun. 11, 1981

[51] Int. Cl.$^3$ .................. A61K 31/70; C07H 15/24
[52] U.S. Cl. .................................. 424/48; 424/49;
424/180; 426/3; 426/552; 426/573; 426/576;
426/590; 426/658; 536/8; 536/117; 536/118;
536/4
[58] Field of Search ............. 536/4, 117, 118, 8,
536/19; 426/658, 576, 590, 552, 573, 3;
424/180, 49, 48

[56] References Cited

U.S. PATENT DOCUMENTS

| | | | |
|---|---|---|---|
| 3,632,804 | 1/1972 | Gray et al. | 536/118 |
| 3,652,541 | 3/1972 | Hjermstad et al. | 536/118 |
| 3,661,890 | 5/1972 | Jurd | 536/8 |
| 3,732,202 | 5/1973 | Jewers et al. | 536/4 |
| 3,756,966 | 9/1973 | Lamberti et al. | 536/4 |
| 4,025,535 | 5/1977 | Crosby et al. | 260/345.2 |
| 4,082,858 | 4/1978 | Morita et al. | 536/4 |
| 4,226,804 | 10/1980 | DuBois et al. | 260/501.11 |
| 4,283,434 | 8/1981 | DuBois et al. | 426/548 |

OTHER PUBLICATIONS

Kohda et al., "Chem. Abst.", vol. 85, 1976, p. 193026z.

*Primary Examiner*—Johnnie R. Brown
*Attorney, Agent, or Firm*—Burns, Doane, Swecker & Mathis

[57] ABSTRACT

Analogs of the glycoside rebaudioside A are disclosed. These materials have the formula

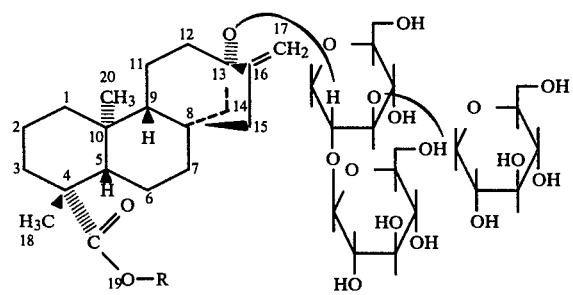

wherein R is a simple physiologically acceptable non-carbohydrate polar organic group. The analogs are sweet and find use as sweeteners.

17 Claims, No Drawings

REBAUDIOSIDE ANALOGS

BACKGROUND OF THE INVENTION

1. Field of the Invention

This invention relates to chemical analogs of the sweet glycoside, rebaudioside A, which are themselves sweet and useful as sweeteners and which do not degrade under conditions of use to form physiologically undesirable steviol as does rebaudioside A.

2. The Prior Art

The leaves of the Paraguayan shrub *Stevia rebaudiana* Bertoni have long been known to be sweet. Several sweet crystalline glycosides have been isolated from these leaves. The principal compound is named stevioside. The secondary compound differs from stevioside in the identity of its saccharide substituent and is known as rebaudioside A. This material has the structure shown in general formula I.

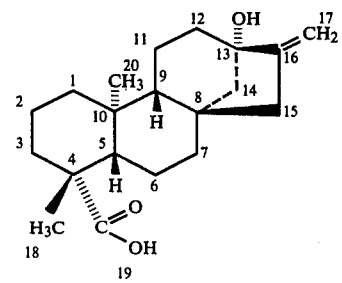

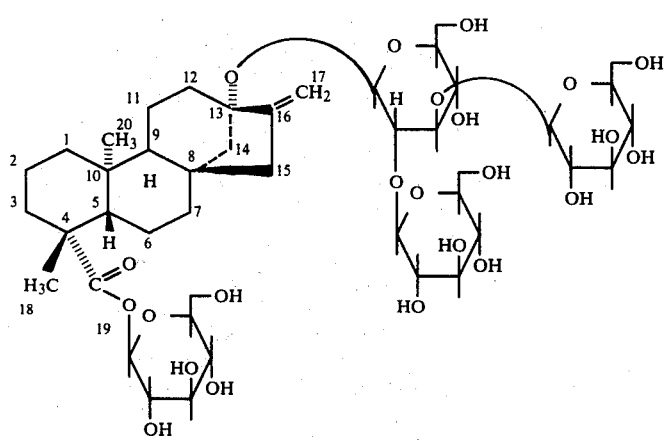

This compound has been identified as a possible sweetener as it provides a relatively sucrose-like intense sweetness. However, it is present in the plant source in small amounts and has not been widely studied.

A threshold question with this material concerns its safety. In 1966, P. V. Vignais and coworkers reported the results of a study concerned with elucidation of the mode of action of the respiratory toxin, atractyligenin. Included in their study were several compounds of related structure including steviol (II), the aglycone of rebaudioside A.

Surprisingly, in cell mitochrondria, steviol was found to be an even more potent inhibitor of ATP synthetase then atractyligenin. (*Biochim. Biophys. Acta*, 118, 465–483 (1966).) In addition, steviol is reported to exhibit antiandrogenic effects (Dorfman, R. I., et al., *Endocrinology*, 67, 282–285 (1965).) Clearly, if rebaudioside A was converted to steviol in vivo, significant toxicity may be expected. Recent results suggest the likelihood that rebaudioside A would be largely converted to steviol in vivo, and further that the steviol thus produced would subsequently be completely absorbed through the gastrointestinal tract wall. (R. Wingard, J. Dale, J. Brown, R. Hale, F. Enderlin, C. T. Seitz, *Experientia*, 36, 519, (1980).) Thus, as a result of a combination of the Vignais and Wingard work, it may be concluded that, with widespread use, rebaudioside A may be expected to exhibit significant acute toxicity. If, however, rebaudioside A's metabolism to steviol could be prevented, that is if a potently sweet analog could be developed which was not degraded to steviol, safety for use in foods would be anticipated.

STATEMENT OF THE INVENTION

A family of new chemical analogs of rebaudioside A has now been discovered. These materials are useful as sweeteners and unexpectedly have the property of being stable to mammalian gastrointestinal tract conditions and not generating steviol in vivo. These compounds have the chemical structures of general formula III

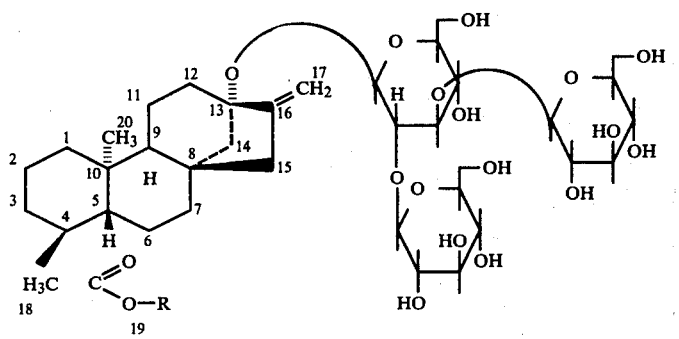

wherein R is a simple noncarbohydrate polar group. These compounds may be further classified as non-glycosidic polar esters of rebaudioside C.

In another aspect, this invention involves the use of these new compounds as sweeteners for comestibles wherein they are admixed with said comestibles.

In yet another aspect, this invention concerns a method for preparing these new compounds and their intermediates.

DETAILED DESCRIPTION OF THE INVENTION

The Compounds

In this Description of the Invention reference will be made to a variety of related diterpenoid compounds. These compounds include:

Rebaudioside A—the natural product shown in general formula I

Steviol—the aglycone of a rebaudioside A shown in general formula II

Rebaudioside C—the base hydrolysis product of rebaudioside A having the structure shown in general formula IV The compounds of this invention differ structurally from art-known rebaudioside A and rebaudioside C in the nature of the "R" substituent on the C-19 oxygen atom. R is a physiologically acceptable noncarbohydrate polar organic group. R should not have oxygen substitution on its α-carbon, that is, it should be α-carbon oxygen free as such substitution in this position is equivalent to hemiacetal or acetal functionality which are unstable in vivo and could lead to formation of steviol. The α-carbon can be a substituted with carboxy, sulfo, phospho, and similar polar groups, however.

R may preferably be selected from among 1 to 10 carbon atom polar organic groups. Preferably, R has from 2 to about 5 carbon atoms. Of necessity, these polar groups will include atoms beyond carbon and hydrogen such as the heteroatoms oxygen, sulfur, nitrogen and phosphorous. These heteroatoms may form anionic or cationic or zwitterionic polar moieties including sulfonate, sulfamate, carboxylate and phosphonate anions, hydroxyls, ammonium cations, and combinations thereof. These polar groups are accompanied by physiologically acceptable counterions. Representative R groups include the materials listed in Table I. Table I also lists precursors or precursor sequences which can be used to insert these R groups as will be set forth herein as Preparative Methods.

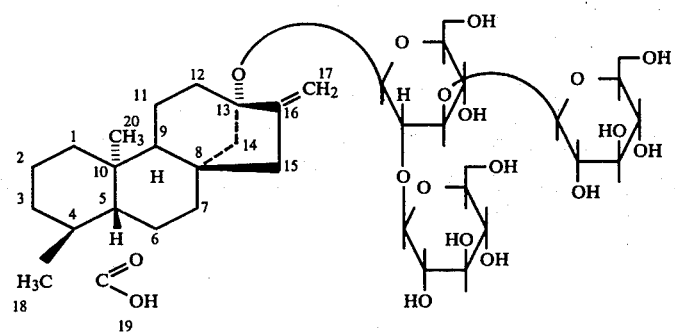

TABLE I

| R GROUP | Precursors |
| --- | --- |
| 1–5 carbon alkyl terminal sulfonates. | $Br-(CH_2)_n-SO_3^-M^+$ |
| $-(CH_2)_n-SO_3^-M^{+*}$ | 1,3-Propane sultone |
| n = 1–5, preferably 2–5, more preferably 3 or 4 and most preferably 3 | 1,4-Butane sultone |
| 1–5 carbon alkyl polysulfonates | $Br-(CH_2)_2-CH(SO_3^-M^+)_2$ |

TABLE I-continued

| R GROUP | Precursors |
|---|---|
| (preferably 2–5 carbons) <br> —$CH_2$—CH—$(SO_3^-M^+)_2$ <br> —$(CH_2)_2$—CH—$(SO_3^-M^+)_2$ <br> —$CH_2$—$CH(SO_3^-M^+)$—$CH_2$—$SO_3^-M^+$ | ![structure] <br> $n = 1,2$ <br> Etc. |
| 1–5 carbon alkyl terminal carboxylates <br> —$(CH_2)_n$—$COO^-M^+$ <br> n = 1–5 preferably 1–3 | Br—$(CH_2)_n$—COOGp* |
| 1–5 carbon alkyl polycarboxylates <br> —$CH(COO^-M^+)$—$(CH_2)_2$—$COO^-M^+$ <br> Etc. | Br—CH—$(COOGp)$—$(CH_2)_2$—COOGp |
| 1–5 carbon alkyl terminal phosphonates <br> —$(CH_2)_n$—$PO_3H^-M^+$ <br> n = 1–5, preferably 2–4 | Br—$(CH_2)_n$—$PO_3(Gp)_2$ |
| 1–5 carbon polyhydroxyls <br> ($CH_2)_{\overline{n}}$ 108 CH(OH)—CH(OH)—$CH_2OH$ <br> ($CH_2)_{\overline{n}}$—CH(OH)—$CH_2OH$ <br> Etc. n = 1,2 | Br—$(CH_2)_n$—CH—$CH_2$ (epoxide) ⟶ <br><br> —$(CH_2)_n$—CH—$CH_2$ (epoxide) $\xrightarrow{H_3O^+/THF}$ <br><br> —$(CH_2)_n$—CH(OH)—$CH_2OH$ <br> or <br><br> Br—$(CH_2)_n$—CH—$CH_2$ (epoxide) $\xrightarrow{H_3O^+/THF}$ <br><br> Br—$(CH_2)_n$—CH(OH)—$CH_2(OH)$ <br><br> $\xrightarrow{2 Ac_2O, pyr}$ <br><br> Br—$(CH_2)_n$—CH(OAC)—$CH_2(OAC)$ |
| 1–5 carbon primary amine salts <br> —$(CH_2)_n$—$NH_3^+X^-$* <br> n = 1–5, preferably 2–4 | Br—$(CH_2)_n$—Br ⟶ <br> —$(CH_2)_n$—Br ⟶ <br> —$(CH_2)_n$—$N_3$ $\xrightarrow[\text{MEOH}]{\text{NaBH}_4 / \text{NiCl}_2 \cdot 6H_2O}$ <br> —$(CH_2)_n$—$NH_3^+Cl^-$ |
| 1–5 carbon alkyl sulfamates <br> —$(CH_2)_n$—NH—$SO_3^-M^+$ <br> n = 1–5, preferably 2–4 | —$(CH_2)_n$—$NH_3^+Cl^-$ $\xrightarrow{Et_3N/DMF,}$ <br><br> ![benzodioxathiole-SO2, MOH] ⟶ <br><br> —$(CH_2)_n$—$NHSO_3^-M^+$ <br> (DuBois and Stephenson, J. Org. Chem. 1980, 45, 5371-3.) |
| 1–5 carbon alkyl amino-carboxylates <br> —$(CH_2)_n$—$CH(NH_3^+)$—$COO^-$ <br> n = 1–4, preferably 2–3 <br><br> —$(CH_2)_n$—$CH(COO^-)$—$(CH_2)_m$—$NH_3^+$ <br> n= 1–2, m = 1–3 | Br—$(CH_2)_n$—CH(NHCOOCH$_2$Ph)COOGp <br><br><br> Br—$(CH_2)_m$—CHBrCOOGp ⟶ |

TABLE I-continued

| R GROUP | Precursors |
|---|---|
| | —CH(COOGp)—(CH$_2$)$_m$—Br $\xrightarrow{\text{NaN}_3}{\text{DMF}}$ |
| | —CH(COOGp)—(CH$_2$)$_m$—N$_3$ $\xrightarrow{\text{KOH}}$ |
| | —CH(COO$^-$K$^+$)—(CH$_2$)$_m$—N$_3$ — $\longrightarrow$ |
| | $\xrightarrow{\text{NaBH}_4, \text{NiCl}_2 \cdot 6\text{H}_2\text{O MeOH}}$ —CH(COO$^-$)—CH$_2$)$_m$—NH$_3$$^+$ |

*M$^+$ = physiologically acceptable alkali metal cation, or alkaline earth metal particularly Na$^+$, K$^+$, Mg$^{++}$ or Ca$^{++}$
*X$^-$ = physiologically acceptable anion such as Cl$^-$
*Gp = protecting group, e.g. —CH$_3$, or —C$_2$H$_5$, or the like that protects a labile functionality and is thereafter removed.

These R groups are merely representative. For example, straight chain materials have been shown but branched materials can be used as well. Other equivalent organic groups may be substituted so long as they are noncarbohydrate and polar.

Among these compounds of this invention preference is given those having 1–5 carbon alkyl terminal sulfonate R groups while among these, the compounds wherein R is —(CH$_2$)$_3$—SO$_3$$^-$K$^+$ or —(CH$_2$)$_3$—SO$_3$$^-$Na$^+$ are more preferred. These two most preferred compounds can be named as rebaudioside C, sulfopropyl ester, potassium and sodium salt.

Preparative Methods

The compounds of the invention can be prepared from art known rebaudioside A by the general preparative scheme of saponifying rebaudioside A to produce rebaudioside C and then reacting rebaudioside C with an "R-addition" reagent, that is a reagent that will add the desired R to the rebaudioside C in place of the hydrogen atom of rebaudioside C's C-19 oxygen atom.

More particularly, the saponification is carried out by reacting rebaudioside A with a molar excess (at least 5 equivalents) of a strong base, especially aqueous or alkanolic or mixed aqueous-alkanolic KOH or NaOH and particularly aqueous and/or methanolic KOH, at elevated temperatures such as from 50° C. to 150° C., preferably 60°–100° C. for a time adequate to effect essentially complete saponification. An especially preferred reaction uses 40–80% methanol as cosolvent as this gives an easily filtrable granular product. At atmospheric pressure this reaction is best carried out at about 65° C., the boiling point of methanol. The concentration of the base is generally from about 1%wt to about 20%wt. The time required would be in the range of from 0.1 hours to 3 hours and would depend upon the temperature employed. At higher temperatures, say 100°–150° C., times from 0.1 to 1 hour are preferred. At lower temperatures, say 50°–100° C., times from 1 to 3 hours are preferred.

Following saponification, the reaction medium is generally neutralized, such as with mineral acid, and the rebaudioside C is recovered. This recovery can be effected by crystallization, brought about by cooling or removal of solvent. The rebaudioside C can be purified by recrystallization, column chromatography or a like process at this point. Such a purification is generally performed.

The rabaudioside C (preferably recovered and purified) is contacted with the "R-addition" agent, under mildly basic conditions to effect addition. The particular "R-addition" agent employed of course depends upon the "R" group sought to be added. A list of exemplary R-addition agents is provided in Table I. In general, any reagent that will displace the rebaudioside C carbonyl group's hydrogen with R, can be used. About 1 equivalent of R-addition agent is used per equivalent of rebaudioside C (preferably 0.9 to 1.1 equivalents). A weak inorganic base, such as an alkali metal or alkaline earth metal carbonate, corresponding to the counterion of the final product (if any), is present in an amount equal to the equivalents of R-addition agent. This reaction is conducted at a low to moderate temperature (0° C. to 30° C., preferably 10°–25° C.) for an extended period such as from 4 to 48 hours, especially from 12 to 48 hours. This reaction is carried out in liquid phase in an aprotic reaction medium, such as dimethylformamide, N-methylpyrrolidone, acetone, dimethyl sulfoxide and the like.

Following reaction with the R-addition agent and neutralization with acid, the product is recovered such as by evaporation, followed by recrystallization. Other equivalent recovery and purification processes may be employed.

These preparative conditions are merely representative. Other equivalent routes may be employed if desired.

Stability of Compounds

An important property of these rebaudioside A analogs is their stability and resistance to conversion to steviol at the conditions of the mammalian gastrointestinal tract. This property is demonstrated in vitro by anaerobically incubating the compounds of the invention with fresh rat cecal contents for three days at 37° C. as detailed in Example 1. At these conditions, no degradation to steviol occurs to a limit of detection of 0.13%. In direct contrast, as reported in the *Experientia* paper of Wingard, et al., noted above, rebaudioside A itself undergoes major degradation to steviol.

Use of the Compounds

The compounds of this invention are useful as sweeteners for comestibles. In this application, they are simply admixed with the comestible by art-known means in dry form or as solutions, preferably in water. They are, advantageously, soluble in water at usual use levels. Representative comestibles include beverages such as sodas, coffee, lemonade, wine and the like; edibles such as gelatin desserts, candy, gum, cakes, cereals and the like, personal products such as mouth wash and toothpaste as well as pharmaceuticals such as cough syrups, and flavored pills.

The compounds of this invention are about 150 to 350 times as sweet as sucrose on a weight basis. Accordingly, the amounts to be employed may be determined by factoring usual sucrose use levels by this 150–350 value. Thus, for example, a soft drink might be sweetened by adding 0.02 to 0.12% by weight of the present compounds. Mixtures of these materials alone or with known other sweeteners (sucrose, saccharin or the like) may also be advantageously employed.

The invention will be further described by the following Examples. These are provided solely to illustrate the invention and are not to be construed as limiting its scope.

EXAMPLE I

Preparation of rebaudioside C, 3-sulfopropyl ester, sodium salt

A. Rebaudioside A (0.2 mmol, 183 mg) was transferred to a 15 ml flask. Four ml each of 10% KOH and methanol were added and the resultant mixture heated to yield a homogeneous solution which was refluxed for 1½ h. Reaction was than judged complete by TLC analysis. After cooling to 0°; the reaction mixture was acidified to pH3 with 10% $H_2SO_4$. The resultant mixture (primarily rebaudioside C) was then concentrated to dryness and the residue recrystallized from water to give 150 mg (99%) of pure rebaudioside C.

B. Rebaudioside C (150 mg; 0.186 mmol) was dissolved in 2 ml of DMF after which 0.20 mmol of $K_2CO_3$ was added along with 0.20 mmol of 1,3-propane sultone. This reaction mixture was stirred under argon for four days at which point silica gel TLC ($CHCl_3$-MeOH-$H_2O$/15-10-2) indicated complete reaction. Excess 1,3-propane sultone was then hydrolyzed by overnight stirring with 10 ml 10% KOH. The reaction mixture was then diluted with water and neutralized with 0.1 N HCl. This mixture was concentrated to dryness and the product separated from KCl by swirling with MeOH and decantation of the low density, product crystals from high density KCl crystals. The MeOH slurry was concentrated to give the crude product as the potassium salt. This material was dissolved in water and converted to the sodium salt by ion exchange on a column of Bio Rad AG MP 50 ion exchange resin. Concentration followed by recrystallization (EtOH-$H_2O$) yielded (145 mg; 82%) the pure rebaudioside C, sulfopropyl ester, sodium salt.

C. A 1000 ppm solution of the subject compound was made up in water and tasted by a group of volunteers. They reported a very intense pure sweet taste which, by comparison to other more completely evaluated sweeteners, was estimated to be about 200–220 times as intense as sucrose on a weight basis.

D. Rebaudioside C, 3-sulfopropyl ester, potassium salt prepared as in Part B. was incubated anaerobically for three days at 37° C. with 5% fresh rat cecal contents at concentrations of 0.25, 0.5, and 1.0 mg/ml, in sterile Krebs-Ringer 0.25 M phosphate buffer (pH 7.4) containing 0.25 mg/ml dithiothreitol and 0.25 mg/ml α-D-glucose. TLC [silica gel F-254; $CHCl_3$:$CH_3OH$:$H_2O$ (15:10:2)] and HPLC [30 cm C-18 on μ-Bondapak; 15 min linear gradient of 10–40% $CH_3CN$ in 0.005 M $KH_2PO_4$ (pH 3.45); 200 nm] analysis showed all the rebaudioside C, 4-sulfopropyl ester ($R_f$=0.42; $t_R$=14.0 min) to have been consumed within 24 h to yield apparently only the sulfopropyl ester of steviol, ($R_f$=0.63;

$t_R$=16.3 min). No steviol ($R_f$=0.95; $t_R$=31.3 min) was detected. After 3 days the bacterial cells were sedimented by centrifugation. The sediment was extracted (THF), as was the lyophilized supernatant. HPLC analysis for steviol of the two THF extracts showed none to be detectable. With a detection limit of 0.05 μg, as little as 0.03 and 0.13 percent degradation to steviol could have been detected for the sediment and supernatant fractions, respectively.

As has been shown above, the sulfopropyl ester moiety is quite stable to the biological conditions which readily degrade the glycosyl ester of rebaudioside A.

E. Use in Comestibles

Based on the results of Part C, one can employ the compound of Part B as a sweetener for comestibles. In exemplary uses 0.08% by weight of the compound is dissolved in an unsweetened cola beverage, a like concentration of the compound is added to an unsweetened lemonade and to coffee. In each case, sweetness is imparted. In two other cases, 0.04% by weight is added to coffee along with 0.02% by weight of saccharin and 3% by weight of sucrose, respectively. Again, sweetness is imparted by the compound of Part B.

EXAMPLE II

A solution of the material of Part B of Example I was passed through an ion exchange column charged with H+. This formed rebaudioside C, 3-sulfopropyl ester. Neutralizing with one equivalent of Ca(OH)$_2$ yeilds the Ca++ salt. Similarly ½ Mg++ could replace K+. When this material is evaluated, as in Parts C, D and E of Example I, it exhibits the same advantageous properties observed with the material of Example I.

EXAMPLE III

Preparation of rebaudioside C, 4-sulfobutyl ester, sodium salt

A. Rebaudioside C (2 mmol) such as from Example I is placed in a 50 ml round bottom flask. DMF (30 ml) is added as is 2.2 mmol of NaH. This mixture was slurried under argon. Then 2.2 mmol of butane sultone is added. The mixture is stirred at 32° C.–37° C. for several days, periodically assaying for reaction completeness by TLC and adding additional NaH and 1,4-butane sultone as required. A product forms and is worked upon by (a) NaOH addition to hydrolyze excess 1,4-butane sultone, (b) dilution to 100 ml with water, (c) titration to pH 6 with $H_2SO_4$, (d) evaporation to dryness, (e) extraction with methanol, recovering and evaporating the extract, and (f) purification of the residual (in methanol) by preparative silica gel chromatography using $CHCl_3$:MeOH:$H_2O$ (80:19:2), and (60:40:2) as eluent. Pure fractions are combined and concentrated to give a solid which on recrystallization (EtOH-$H_2O$) yields rebaudioside C, 4-sulfobutylester, sodium salt as colorless clusters.

B. When tested, this material is observed to be sweet, like the material of Example I.

EXAMPLE IV

Preparation of a compound wherein
R=—$CH_2$—$CH_2$—$NH_3$+Cl−

Rebaudioside C (1 mmole) and $K_2CO_3$ (2 mmol) were added with 10 ml of distilled DMF to a 25 ml flask under argon. 1,2-dibromoethane (10 mmol) is then added and the mixture stirred at 40° C. overnight. The next morning the reaction is judged complete by TLC assay to yield rebaudioside C, 2-bromoethyl ester. This material is mixed with 40 mmol of NaN$_3$ and stirred overnight at about 25° C. to convert to the 2-azidoethyl ester. This reaction product is added to 50 ml of 1% HCl at which point a solid forms and is recovered by filtration, and dried. This dry product (0.2 mmol) is dissolved in 10 ml CH$_3$OH, 10 ml THF and 1.5 ml CHCl$_3$ and mixed with 25 mg of 5% Pd on BaSO$_4$. Hydrogen is bubbled through the reaction at 5° C. overnight. Later the reaction mixture is warmed to room temperature. When TLC checks showed no further reaction, the solution is filtered through a millipore filter, evaporated to dryness, dissolved in water, filtered and evaporated to dryness to give rebaudioside C, 2-aminoethyl ester, hydrochloride.

EXAMPLE V

Preparation of compound wherein R equals
—CH(COOH)—CH$_2$—CH$_2$—COOH

Rebaudioside C (5 mmol) is dissolved in 20 ml of dry DMF under argon. K$_2$CO$_3$ (6.2 mmol) is then added with 20 ml DMF. and 6.2 mmol of Br—CH(COOCH$_3$)—CH$_2$—CH$_2$—COOCH$_3$. The mixture is stirred at room temperature for several days, after which, reaction is complete. The mixture is worked up by HCl addition (to pH 6.5) solvent evaporation, followed by column silica gel chromatography using CHCl$_3$—MeOH as eluent. A product, wherein R=—CH(COOCH$_3$)—CH$_2$—CH$_2$—COOCH$_3$ is recovered off the column. This product is hydrolyzed by adding 50 ml of methanol and 50 ml of 10% KOH and stirring at room temperature for 30 minutes to effect conversion to the desired diacid salt. This product is neutralized with HCl, filtered and recrystallized from acetone:methanol 100:1. This yields the desired diacid.

This material is sweet and can be used to sweeten comestibles.

EXAMPLE VI

Preparation of compound wherein R equals
—CH$_2$—CH$_2$—CH(NH$_3^+$)—COO$^-$

The "R-addition agent", Br—(CH$_2$)$_2$—CH—(-COO—CH$_3$)—NH—COOCH$_2$Ph is obtained as shown in Example I of DuBois et al U.S. Pat. No. 4,226,804 which is incorporated by reference.

Rebaudioside C (2.0 mmol), K$_2$CO$_3$ (2.5 mmol) and R addition agent (2.5 mmol) are placed in a flask with 25 ml of dry DMF under argon and stirred at room temperature overnight. The addition reaction appears complete by TLC. The product is extracted with ethylacetate. The extracts are washed, dryed and evaporated to yield a solid product.

The solid product is then dissolved in 30 ml of methanol and 30 ml of 10% NaOH and heated to reflux. It is refluxed until no starting material is left by HPLC. The methanol is then evaporated and the remaining product titrated to pH 6.0 with 2 N H$_2$SO$_4$, and then evaporated to dryness. The solid is extracted with boiling methanol and the extracts concentrated to yield the desired solid product.

This material is sweet and sucrose like.

EXAMPLE VII

Preparation of Rebaudioside C ester where R is
—CH$_2$—COONa

A. Rebaudioside C (2 mmol), K$_2$CO$_3$ (2.5 mmol) and 20 ml of dry DMF are placed in a flask under argon and mixed into solution. Ethylchloroacetate (2.5 mmol) is added and the mixture is stirred at 43° C. for seven hours. The reaction appears complete by TLC so it is cooled and worked up by addition to excess chilled 5% HCl whereupon a precipitate formed that was recovered by filtration. This product had as its C-19 oxygen substituent, —CH$_2$—CO$_2$—C$_2$H$_5$.

B. The ethyl protecting group is hydrolyzed by treatment with 10% KOH until TLC assay shows reaction completion. The product is precipitated on acidification (10% HCl) to pH3 and is isolated by filtration. The product is dissolved in 1.00 equivalents NaOH and the resultant solution lyophilized. Recrystallization (MeOH) yields the desired rebaudioside C, carboxymethyl ester, sodium salt.

C. This material is sweet when tasted by a group of volunteers.

EXAMPLE VIII

Preparation of Compound where R equals
—CH$_2$—CH$_2$—CH(SO$_3^-$)$_2$Na$_2^+$

A. Propane sultone (1.00 mmol) and 2.0 ml of dry THF were placed in a round bottomed flask. n-butyl lithium (1.10 mmol of 2.4 M solution) was then added dropwise over five minutes while stirring vigorously under argon and cooling at −78° C. the mixture was stirred for about five minutes and 1.10 mmol of

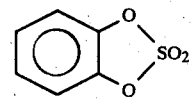

was added along with 2.0 ml of THF, and this mixture was stirred at −78° C. for 30 minutes.

The product was worked up by being added to 20 ml of ice/10% HCl; saturated with NaCl, and extracted twice with diethyl ether. The extracts were dried and concentrated to yield the crude product as an oil. This oil was purified by passage through silica gel, washing with CHCl$_3$-MeOH, and rotary plate thin layer chromatography. The identity of the desired product

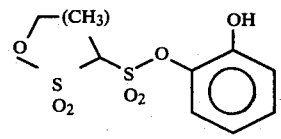

was confirmed by IR and NMR analysis.

B. Rebaudioside C (2.7 mmol) is dissolved in about 20 ml of dry DMF. 5.2 ml of 0.51 M Potassium-amyloxide-toluene solution (2.7 mmol) is then added. The R-addition agent of Part A (2.7 mmol) is added and stirred at room temperature for 72 hours. The reaction mixture is evaporated to yield residue which is dissolved in 25 ml of water and brought to pH6 with HCl. This gives a solid upon evaporation which is dissolved in methanol and purified by rotary silica gel chromatography. The desired product is isolated and recrystallized from methanol/water.

C. The solid (0.90 mmol) of part B is dissolved in 100 ml of distilled water under argon. 1.40 mmol of 0.11 M KOH is added and the mixture refluxed for 7 hours. The reaction is cooled, neutralized and concentrated to dryness to yield a solid. This product is then dissolved in water, purified by rotary silica gel chromatography and converted to the sodium salt by ion exchange chromatography and recrystallized to produce crystals of the rebaudioside C ester compound wherein R is —CH$_2$—CH$_2$—CH(SO$_3^-$)$_2$Na$_2^+$.

D. The compound of part C is dissolved in distilled water at a concentration of 1000 ppm by weight. It is exceedingly sweet, at least equal in intensity to a 10–12% sucrose solution.

EXAMPLE IX

It will be appreciated that the sweeteners of the invention can be incorporated into a wide range of comestibles.

Cups of coffee are prepared: To each is added 500 ppm by weight, basis solution, of one of each of the sweeteners prepared in Examples II–VIII. The coffees present a sweetened taste when sampled.

Gelatin, food color and fruit flavor are dissolved in water at levels suitable for forming a jelled food product. The solution is not sweet. The materials of Claims II–VIII are each added to separate samples in amounts of 600 ppm and the samples are cast into jelled products. The resulting gelatin products are sweet.

What is claimed is:

1. A nonglycosidic polar ester compound of rebaudioside C having the structure

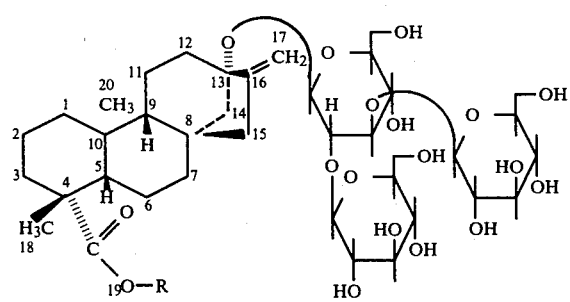

wherein R is a physiologically acceptable noncarbohydrate polar organic group that is α-carbon oxygen free and that contains from 1 to 10 carbon atoms inclusive.

2. A rebaudioside C analog compound having the structure

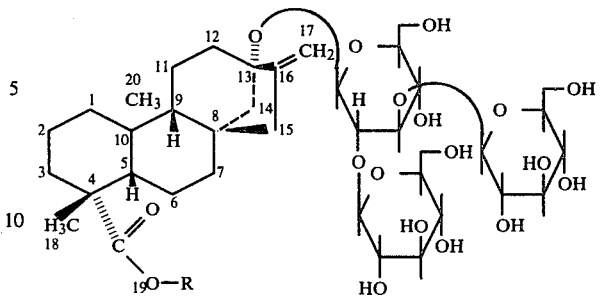

wherein R is a physiologically acceptable noncarbohydrate polar organic group that is α-carbon oxygen free and that contains from one to ten carbon atoms inclusive and one or more polar moiety selected from sulfonate, sulfamate, carboxylate, and phosphate anions, ammonium cations and hydroxyl groups.

3. The compound of claim 2 wherein R is a 1 to 5 carbon inclusive alkyl terminal sulfonate salt.

4. The compound of claim 3 wherein R is of the formula

—(CH$_2$)$_n$—SO$_3^-$M$^+$ wherein n is an integer from 2 to 5 inclusive and M$^+$ is a physiologically acceptable alkaline earth metal cation or alkali metal cation.

5. The compound of claim 4 wherein n is 3 or 4 and M$^+$ is selected from Na$^+$, K$^+$, ½ Ca$^{++}$ and ½ Mg$^{++}$.

6. The compound of claim 5 wherein n is 3 and M$^+$ is Na$^+$ or K$^+$.

7. The compound of claim 2 wherein R is a 1 to 5 carbon inclusive alkyl polysulfonate.

8. The compound of claim 7 wherein R has the formula

—(CH$_2$)—CH—(SO$_3^-$)$_2$M$^+$$_2$

M$^+$ is a physiologically acceptable alkaline earth metal cation or alkali metal cation, and n is an integer of from 1 to 2 inclusive.

9. The compound of claim 2 wherein R is a 1 to 5 carbon atom alkyl terminal carboxylate of the formula —(CH$_2$)$_n$—COO$^-$M$^+$ and n is an integer from 1 to 5 inclusive and M$^+$ is a physiologically acceptable alkaline earth metal cation or alkali metal cation.

10. The compound of claim 2 wherein R is a alkyl terminal phosphonate of the formula —(CH$_2$)$_n$—PO$_3$H$^-$ M$^+$ and n is an integer from 1 through 5 inclusive and M$^+$ is a physiologically acceptable alkaline earth metal cation or alkali metal cation.

11. The compound of claim 2 wherein R is a 1 through 5 carbon inclusive linear alkyl polycarboxylate.

12. The compound of claim 2 wherein R is a 1 through 5 carbon inclusive linear polyhydroxyl alkyl.

13. The compound of claim 2 wherein R is a 1 through 5 carbon inclusive primary alkyl amine salt.

14. The compound of claim 3 wherein R is a 1 through 5 carbon inclusive alkyl polysulfonate.

15. The compound of claim 2 wherein R is a 2 through 5 carbon inclusive alkyl amino carboxylate.

16. A sweet comestible comprising an edible material admixed with an effective sweetening amount of the compound of claim 1.

17. In the process for converting rebaudioside A to rebaudioside C which comprises treating rebaudioside A with a molar excess of alkali metal hydroxide in a liquid phase reaction medium at an elevated temperature, the improvement comprising employing as said medium a liquid comprising water and 40–80% methanol and as said elevated temperature, 60° to 100° C.

* * * * *